United States Patent [19]
Rosenberg

[11] Patent Number: 5,324,276
[45] Date of Patent: Jun. 28, 1994

[54] DEVICE AND METHOD FOR INHIBITING INTRAVASCULAR DEVICE ASSOCIATED INFECTION

[76] Inventor: Paul H. Rosenberg, 1600 Parker Ave., Fort Lee, N.J. 07024

[21] Appl. No.: 2,585

[22] Filed: Jan. 11, 1993

Related U.S. Application Data

[63] Continuation-in-part of Ser. No. 694,109, May 1, 1991, Pat. No. 5,178,611.

[51] Int. Cl.[5] .................. A61M 25/00; A61M 5/00
[52] U.S. Cl. .................. 604/269; 604/264; 604/280; 604/172
[58] Field of Search ........... 604/264, 265, 266, 267, 604/268, 269, 280, 284, 164, 167, 172, 49, 51, 53

[56] References Cited

U.S. PATENT DOCUMENTS

| | | | |
|---|---|---|---|
| 4,717,379 | 1/1988 | Ekholmer | 604/280 |
| 4,781,678 | 11/1988 | de Cou et al. | 604/266 |
| 4,968,306 | 11/1990 | Huss et al. | 604/264 |

FOREIGN PATENT DOCUMENTS

| | | | |
|---|---|---|---|
| 0284322 | 9/1988 | European Pat. Off. | 604/266 |
| 8500526 | 2/1985 | World Int. Prop. O. | 604/266 |
| 49201 | 1/1992 | World Int. Prop. O. | 604/269 |

*Primary Examiner*—John G. Weiss
*Attorney, Agent, or Firm*—Cohen, Pontani, Lieberman, Pavane

[57] ABSTRACT

The present invention is directed to a device for reducing the risk of infection and/or clotting associated with the establishment and/or maintenance of fluid communication between apparatus external to the body and the interior of the body. The device includes a first tube insertable into the body. A second tube is disposed within the first tube, the second tube having a distal end portion insertable into the body and extending through an opening defined at the distal end of the first tube. The first and second tubes define therebetween a longitudinally coaxially disposed channel which establishes a fluid communication path for a first fluid. The first tube has one or more predeterminately-sized capillary apertures defined therein and predeterminately sized so as to predeterminately control the flow of a first fluid through the aperture, so that the first fluid remains substantially on and along the outer surface of the first tube so as to coat the outer surface of the first tube with the first fluid, thereby creating an anti-infective barrier which surrounds the intravascular device as it lies within the body. The second tube may also or alternatively include apertures for the selective coating and/or irrigation of the interior of the second tube to prevent infection or clotting therein.

20 Claims, 6 Drawing Sheets

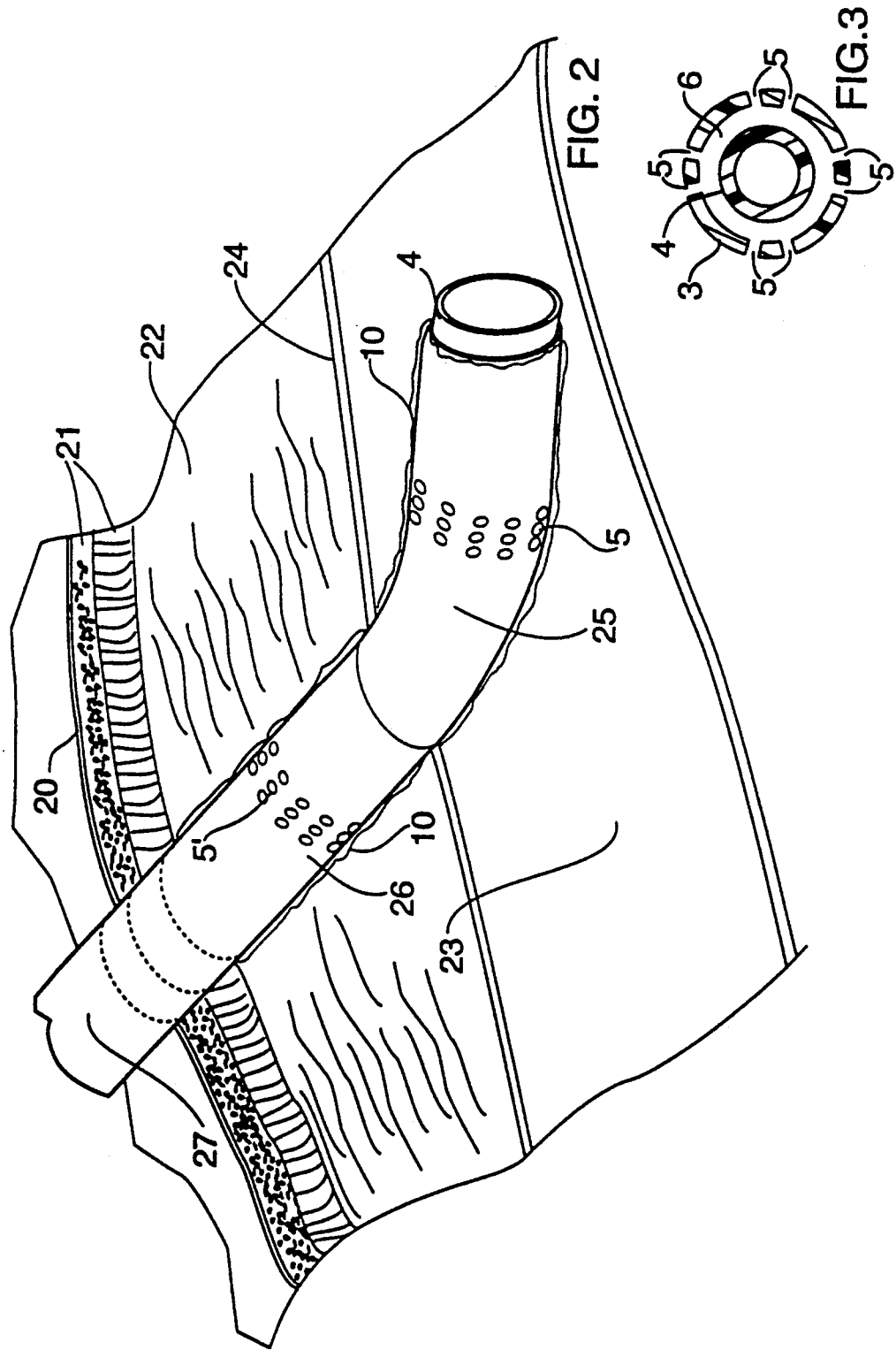

DEVICE AND METHOD FOR INHIBITING INTRAVASCULAR DEVICE ASSOCIATED INFECTION

CROSS REFERENCE TO RELATED APPLICATIONS

This application is a continuation-in-part of application Ser. No. 07/694,109, filed May 1, 1991 now U.S. Pat. No. 5,178,611.

FIELD OF THE INVENTION

The present invention relates to a device and method for reducing the risk of infection and clotting associated with the establishment and/or maintenance of fluid communication between apparatus external to the body and a blood vessel, organ or other site within the body.

BACKGROUND OF THE INVENTION

Cathers are currently used for a variety of medical purposes in a wide range of both diagnostic and therapeutic applications. Catheters are, by way of example, most commonly used in the peripheral blood vessels (i.e. those close to the skin) to support and maintain blood volume levels, to introduce medications into the blood stream, and to provide nutritional support. Catheters are also used in arterial vessels to monitor certain blood parameters and to deliver regional chemotherapy. Connections to veins deep within the body may be established to obtain localized blood samples, to deliver nutritional compounds, to measure cardiac output and, in some cases, may be implanted on a semi-permanent basis to deliver chemotherapeutic compounds or to maintain a continuous mode of central venous access. Catheters are also commonly used in the urinary tract.

While the foregoing listing is far from exclusive, each of these utilities is associated with a substantial risk of infection or clotting in and around the catheter, particularly where the catheter remains in situ for an extended period of time. While the exact causes of all such complications are not completely known, conventional efforts to reduce or eliminate intravascular device-associated infection presently take several forms. The first usually involves pre-insertion cleansing of the skin surface surrounding the area of penetration to prevent contamination of the device as it penetrates the skin by infectious agents which are present on the skin surface. Regular removal and replacement of the intravascular device every two to three days, for example, is also a common anti-infective procedure. Furthermore, different materials such as Telfon (PTFE) and polyvinylchloride (PVC) have been used in the manufacture of catheters, each having demonstrated some ability to prevent the onset of infection by discouraging infectious agents from adhering to and growing on the catheter surface. More recently, catheters have also become available with anti-microbial agents bonded to the exterior surface of the catheter. None of these currently known devices or procedures, however, has proven to be sufficiently effective successful in preventing the onset of infection or clotting within the catheter, or on or along the exterior portions of the catheter that extend into the body.

OBJECTS AND SUMMARY OF THE INVENTION

It is accordingly a particular object of the present invention to provide a catheter useful for a variety of conventional applications while providing a significantly reduced risk of infection over presently known catheters.

It is a further object of the invention to provide an intravascular device and method which can be used to reduce the risk of infection not only at the location at which the device resides within the blood vessel but, in addition, at locations remote from the blood vessel such, for example, as at the interface between the catheter peripheral surface and the surrounding body tissue, or along the interior surface of the cannula forming the lumen.

It is another object of the invention to provide a catheter device and method for preventing accumulations of clots within the catheter fluid delivery pumps and for maintaining a free and unimpeded flow of delivery fluid or medication or the like to or from the body situs to which the catheter is inserted.

The present invention provides, in accordance with the foregoing objects, an intravascular device or catheter comprising, in an embodiment herein disclosed, an outer tube which is inserted through the skin into a blood vessel and an inner tube which is inserted coaxially through the outer tube and also extends into the blood vessel. The inner tube extends beyond the distal termination of the outer tube which sealingly engages the inner tube at the termination of the former. The annular channel formed between the inner and outer tubes provides a fluid communication channel for a first fluid, while the inner tube provides an additional fluid communication path for a second fluid. The first fluid—which may be an anti-microbial agent or the like—is delivered through the channel onto the outer surface of the catheter via small capillary-like apertures which are defined in and through and, optionally, distributed along the outer surface of the outer tube. The apertures are predeterminately sized so that when the first fluid is delivered outwardly from the channel through the capillary apertures, it adheres to and coats the exterior peripheral surface of that portion of the outer tube which extends within the body, thereby creating an effective anti-infection barrier along the exterior surface of the second tube. In this manner the risk of infection along the exterior surface of the catheter while it is positioned in situ within the body is significantly reduced.

Alternatively, or additionally, fluid may be delivered through the fluid communication channel to the interior wall surface of the inner tube through apertures defined in and through the inner tube, to medicate, and/or to flush and irrigate, the interior of the inner tube for preventing infection and/or clotting therein.

In another embodiment, the catheter may be formed of three coaxially disposed tubes, namely an outer, a middle and an inner tube, thereby defining two annular fluid communication channels in concentric relation. The first channel is formed between the outer and middle tubes and functions to communicate fluid to the outer surface of the catheter through the above-referenced capillary apertures. The second channel is formed between the inner and middle tubes and functions to communicate fluid to the inner wall surface of the inner tube through the aforementioned inner tube apertures, for the beneficial purposes mentioned above.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote similar elements throughout the several views:

FIG. 2 is an enlarged, cross-sectional side view similar to FIG. 1 and depicting that portion of the catheter device that is inserted into the body and the coating action of the first (e.g. anti-microbial) fluid;

FIG. 3 is a cross-sectional view taken along the lines 3—3 in FIG. 1;

DETAILED DESCRIPTION OF THE PREFERRED EMBODIMENTS

Figure 4:
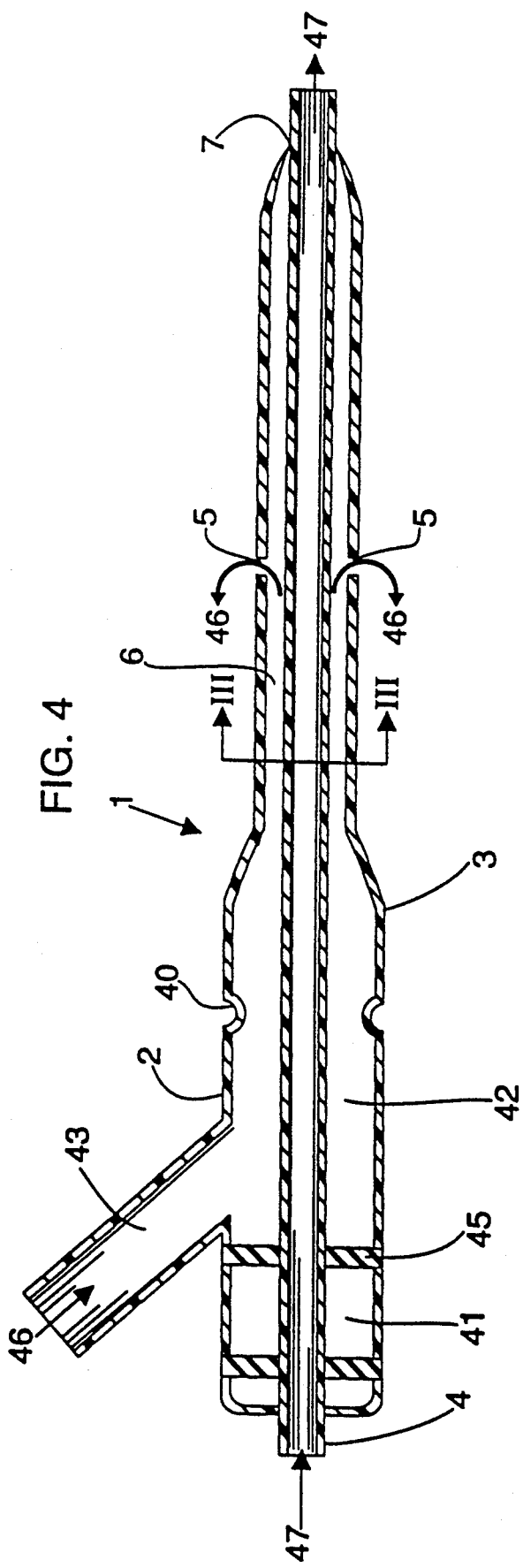
FIG. 4 is a cross-sectional side view of the catheter of FIG. 1 depicting the relationship of the inner and outer tubes and the formation of the annular fluid communication channel therebetween.

With initial reference to FIG. 4 which illustrates a cutaway side view of a catheter-type intravascular device 1 constructed in accordance with the present invention, the device 1 includes a first or outer tube 3. Positioned within and in longitudinally coaxial relation to outer tube 3 lies a second or inner tube 4. The outer diameter of the second tube 4 is smaller than the inner diameter of outer tube 3, thereby forming a coaxially annular channel 6 in the space between the two tubes. Outer tube 3 terminates in an opening 7 through which the second tube 4 extends. The first tube 3 is narrowed or tapered in the region of the opening 7 whereby the first tube 3 sealingly engages the second tube 4, creating a fluid barrier which effectively closes and terminates the channel 6. The channel 6 forms a fluid communication path 46 for a first fluid whereas the second tube 4 forms a second fluid communication path 47 for a second fluid. Positioned along and through the outer surface of the first tube 3 are a plurality of small capillary apertures 5. These apertures are in direct fluid communication with the channel 6, thereby enabling a first fluid 10 to be delivered outwardly from the channel 6 to and onto the outer surface of the first tube 3. The coaxial relationship of the first and second tubes, and the formation of the coaxially annular fluid communication channel 6 defined between the first and second tubes, are shown in detail in the sectional view of FIG. 3.

Also depicted in FIG. 4 is a hub unit 2 which provides a mechanism for connecting the first tube 3 and the second tube 4 to external apparatus for delivery of the first and second fluids. The hub unit comprises a central region divided into a first branch 41 and a second branch 42. The second branch 42 is in fluid communication with a third branch 43 which extends at an angle away from the first and second branches. Within the first branch 41 are seals 45 which sealingly engage the second tube 4 when the second tube 4 is positioned within the hub 2. Seal 45 engages the second tube 4 to create a fluid tight barrier whereby the second branch 42 and third branch 43 form a continuous fluid communication path that leads to the fluid communication channel 6 formed in the coaxial clearance or space between the outer face of the second tube 4 and the inner periphery or face of the first tube 3. The first fluid communication path 46 permits delivery of first fluid from an external apparatus connected to the third branch 43, through the second branch 42, further through the channel 6, and out through the capillary apertures 5. Additionally illustrated in FIG. 4 is a groove 40 which extends circumferentially around the outside surface of the hub 2. The groove 40 provides a retaining means for a skin-engaging suture (not shown) which may be used to secure the hub to the surface of the skin and thereby maintain precise relative positioning of the inventive device while its tubes 3, 4 are inserted through the skin and into a blood vessel.

Figure 1:
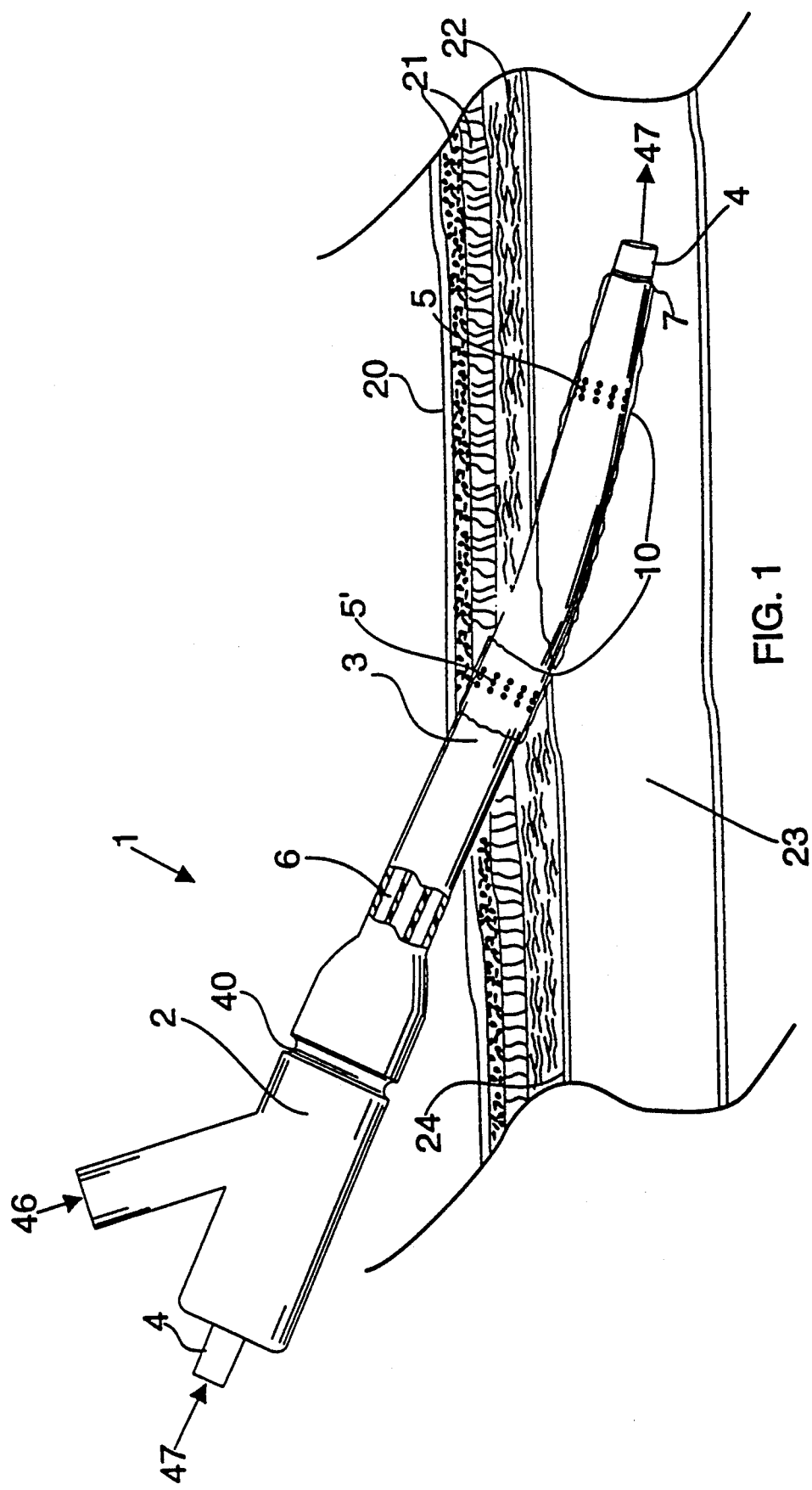
FIG. 1 is a side view, partly in cross-section, of a catheter constructed in accordance with the present invention and shown in operative position extending through the skin and body tissue and into a blood vessel.

FIG. 1 shows the catheter-type intravascular device 1 of the invention in use and, more particularly, operatively inserted into a blood vessel 23. As there shown, the device 1 is extended through the skin surface 20, through the layers of skin 21 surrounding the blood vessel, through the surrounding tissue 22 about or proximate the blood vessel, and through the blood vessel wall 24. The first and second tubes 3, 4 are assembled such that the second tube 4 is positioned within the first tube 3, and the second tube 3 is then extended into the blood vessel 23 through an opening 7 in the distal end of the first tube 3. The longitudinally coaxial relationship of the first and second tubes defines the coaxially annular fluid communication channel 6 in the space or clearance between the two tubes and thereby forms the fluid communication path 46 for the first fluid 10. The second tube 4 forms the second fluid communication path 47 for the second fluid. The first and second tubes are preferably capable of longitudinal movement relative to each other, thereby permitting precise positioning of the tubes within the body and, in suitable applications, to provide for selective replacement of the second tube 4 while the first tube 3 remains positioned in the blood vessel.

In one currently contemplated mode of use, the first tube 3 is inserted through the skin and into the blood vessel, and is there properly positioned, and the second tube 4 is then inserted through the first tube thereby also positioning the second tube in the blood vessel. After positioning the tubes 3, 4, two fluid paths are formed for fluid communication with the blood vessel. The second tube 4 is used in the manner of any standard catheter, either feeding or infusing fluids into or withdrawing fluids from the blood vessel. The first tube 3, however, is used to deliver an anti-infective agent into the channel 6 and outwardly through the capillary apertures 5 and 5' which are positioned along and through the first tube 3. The predeterminately sized capillary apertures 5, 5' may, for example, be formed as small circular openings as shown in FIG. 2, said predetermined size of said capillary aperture being selected for predeterminately controlling the flow of the first fluid through said aperture so that as the first fluid is delivered outwardly from said channel through said aperture, the first fluid remains substantially on and along the outer peripheral surface of said first tube proximate its distal end portion so as to coat said distal end portion of the first tube with the first fluid and thereby create an anti-infective barrier on and along the first tube outer peripheral surface disposed within the body. Each circular opening is sized small enough to release the first fluid in a capillary-like fashion. That is, the fluid moves through the small opening and continues out and along the outer surface of the tube, instead of being ejected outward and away from the tube, so that when the first fluid 10 is delivered from the channel 6 through the apertures 5, 5' the fluid 10 remains on and along and adheres to and coats the outer surface of the first tube 3. The principle by which this coating action occurs is known in the art, and results from a tendency of fluids ejected through sufficiently small openings to form individual bubbles which coalesce, adhere to and coat the outer surface of a tube from which the fluid is discharged. This coating acts as an anti-infective barrier, greatly inhibiting the growth of infectious organisms along the surface of the inserted device. The first fluid 10 may be, for example, a lubricant, an anti-clotting agent, saline or a medicament fluid selected from any of a number of commonly used anti-infective or anti-microbial agents such as, for example, a non-specific, anti-microbial organic short chain fatty acid. The second tube 4 provides a fluid communication path 47 for a second fluid to be delivered into the blood stream in a conventional manner known and used in traditional catheters.

FIG. 2 depicts the inventive device 1 in use and operatively inserted into a blood vessel 23, and shows in greater detail the skin layers 21 and tissue layer 22 surrounding the blood vessel 23. It also shows that 3 regions into which the device 1 can, for ease of description and discussion, be separated. The first region is the first tube distal end first region 25. This is the region which remains within the interior of the blood vessel while the device 1 is inserted. The second region is the first tube distal end second region 26. This is the region which extends proximally (i.e. upwardly in FIG. 2) from the wall of the blood vessel 24 but remaining beneath (or at least not extending outwardly beyond) the surface of the skin 20. The third and final region is the first tube proximal region 27 which extends beyond and outside of the skin surface 20. The capillary apertures 5 are distributed along the outer surface of the first tube distal end first region 25. When the first fluid 10 is caused to flow through the channel 6 and out through the capillary apertures 5, the first fluid 10 will coat the outer surface of the first tube along at least the first tube distal end first region 25. In this way an anti-infective barrier is caused to form along the outer surface of the first tube distal end first region 25, thus inhibiting the growth of infectious agents or the like or infection along that portion of the device 1 which lies within the blood vessel 23.

The first fluid 10 may also be caused to flow through the channel 6 and outward through capillary apertures 5', thus causing the first fluid 10 to additionally or alternatively form a coating along the outer surface of the first tube distal end second region 26. This effectively forms an anti-infective barrier in the region which starts proximate the blood vessel wall 24 and which ends at or beneath the skin surface 20. In this way an anti-infective barrier may be created along the outer surface of the device 1 as it extends through the skin layers 21 and the surrounding tissue 22 around the blood vessel 23.

As can be seen from the foregoing, the first fluid may be delivered so as to coat substantially the entire outer surface of the device which is disposed beneath the surface of the skin and within a blood vessel, thereby greatly reducing the risk of infection both within the blood vessel and, in addition, in the skin and tissue immediately surrounding the blood vessel. The device may be configured so as to provide the capillary apertures only in the first tube distal end first region 25 as denoted by the apertures 5, or solely in the first distal end second region 26, as indicated by the apertures 5', or in both regions simultaneously. The choice will depend, at least in part, on the critically and other aspects of the application to which the device is applied, as well as on any particular anti-infective measures otherwise required.

Figure 5:
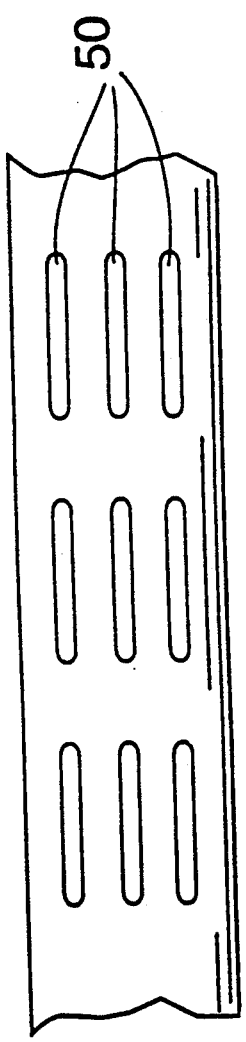
FIGS. 5 and 6 depict alternate configurations and locations of the capillary apertures defined in and through the outer tube of the inventive catheter.

FIG. 5 depicts an alternative configuration for the capillary apertures. As seen by way of example in FIG. 5, the capillary apertures may be shaped as elongated, longitudinally disposed slits 50 which are distributed along the outer surface of the first tube 3. These elongated, longitudinally disposed slits must, in accordance with the invention, be predeterminately sized so as to create the previously mentioned coalescence of the first fluid 10 along the outer surface of the first tube 3 as the first fluid is discharged from the fluid communication path 46.

Figure 6:
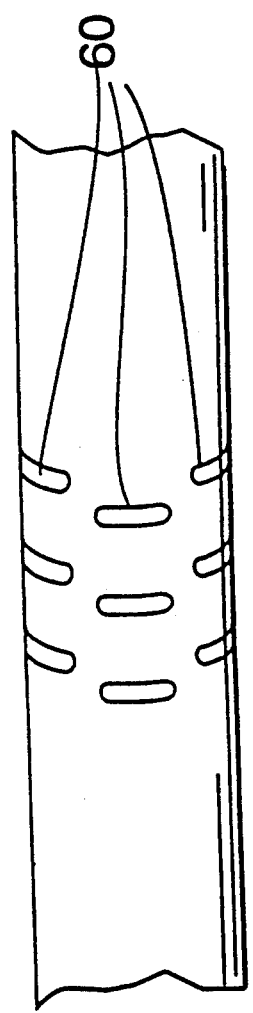

FIG. 6 illustrates a further alternative configuration for the capillary apertures. In FIG. 6, the capillary apertures are shown as elongated slits 60 oriented transverse to the longitudinal axis of the first tube 3. These elongated transverse slits 60 must, once again, be predeterminately sized so as to create the previously mentioned coalescence of the anti-infective first fluid 10 along the outer surface of the first tube 3.

As will now be apparent from the foregoing description and associated drawings, the inventive device serves the traditional function of an intravenous catheter whereby a second fluid may be introduced into the blood stream through the second fluid communication path 47 from an external apparatus. By additionally providing a first fluid communication path 46 through which an anti-infective agent is deliverable via the channel 6 and the apertures 5, 5', a prophylactic coating may be formed along the outside surface of the catheter as it is inserted and while it remains in situ beneath the surface of the skin and within the blood vessel, thereby allowing it to be left in place for extended periods of time without the risk of infection currently associated with such inserted devices. It should also be recognized that the second tube 4 can be removed and replaced or reinserted while the first tube remains in place, without the necessity of removing the first tube. This provides the additional flexibility of modifying or changing the characteristics of the second fluid communication path 47, and allows delivery of alternate second fluids through the second tube along the second fluid communication path 47.

Figure 7:
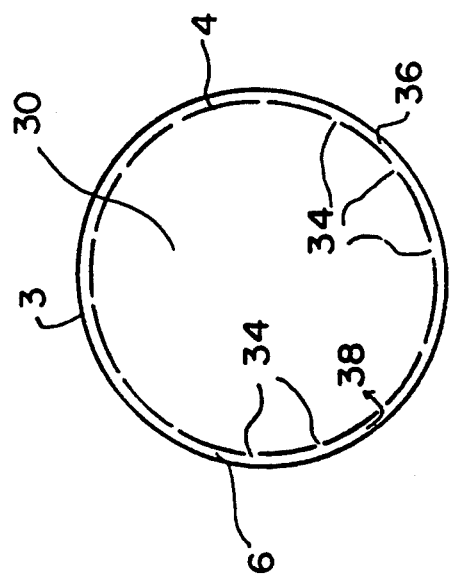

In another preferred embodiment, and with particular reference to the cross-section of FIG. 7, the catheter may be formed so as to alternatively communicate fluid to the interior of the catheter by forming alternate apertures 34 in and through the wall of the second or inner tube 4 to form an alternate fluid communication path 38 from the channel 6 through alternate apertures 34 and into the interior, or lumen, of the second tube 4. By enabling fluid delivery from the channel 6 to the interior of the second tube 4, neutral or medicament solutions may be substantially and/or gradually delivered directly into the second tube to prevent the accumulation or collection of infectious agents or other substances within the catheter, and/or to flush the tube interior to prevent the formation or buildup of clots therein. The apertures 34 may be formed as capillary apertures similar to apertures 5 and 5' to allow for the substantial coating of the interior surface of the second tube 4, or the apertures 34 may be sized and shaped to permit effective flushing or irrigation of the interior of the second tube 4. The fluid may be any of the above described anti-infective agents, or saline, free water or, for example, the anti-clotting agent heparin. The fluid is delivered at a pressure sufficient to cause the pressure in the channel 6 to be, at least as great as, and more typically greater than, that in the interior of the second tube 4. In common applications, it is contemplated that the fluids feeding the catheter be provided from traditional IV bags or bottles, and the required pressure or pressure differential can be adequately achieved by elevating the IV source feeding the channel 6 to a height equal to or greater than the height of the IV source feeding the second tube 4 so as to achieve the desired fluid flow through the communication path 38. Of course, other means of providing a pressure equality or difference, such as motorized or manual pumps, are also contemplated and are within the intended scope of the invention.

Figure 8:
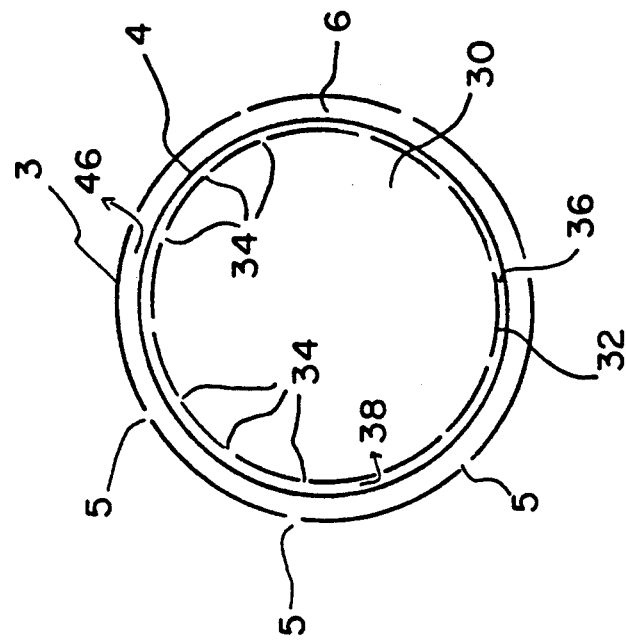
FIGS. 7, 8 and 9 depict cross-sectional views of further alternative embodiments of the inventive catheter depicting configurations of the tubes and apertures so disposed as to provide an alternate or additional fluid communication path to the interior of the catheter through apertures defined in and through the inner tube.

In a further alternative embodiment, depicted in FIG. 8, the catheter is so constructed as to permit selective introduction of fluids to both the external and interior surfaces of the catheter. This is achieved by positioning a third tube 32 within the second tube 4, in longitudinally coaxial alignment therewith, so as to form a second annular channel 36. Annular channel 36 serves to form an additional fluid communication path 38 for the delivery of fluids to the interior of the catheter as described above. In this embodiment the same or different fluids, for example anti-infective and/or anti-clotting agents, lubricants or flushing agents, may be alternately or concurrently delivered as desired to both the catheter exterior and interior to enhance safe, short or long-term placement of the catheter in the body. The pressure required to permit the intended passage of fluids through the communication paths 38 and 46 may be readily achieved by the means and procedures described above.

Figure 9:
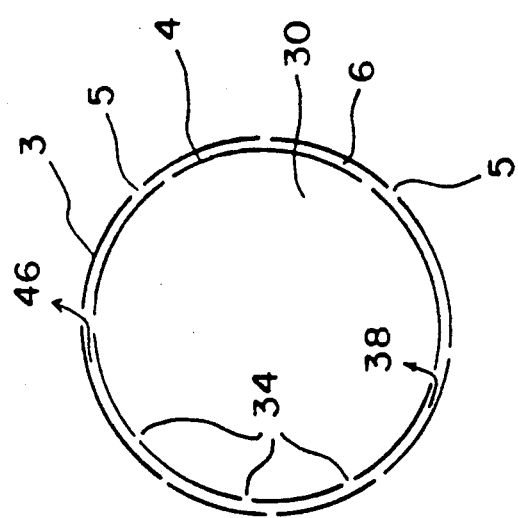

In a further alternative embodiment, depicted in FIG. 9, each of the tubes 3 and 4 are respectively configured with apertures 5 and 34. The channel 6 defined between the tubes delivers fluid simultaneously through the apertures via fluid communication paths 38 and 46, permitting the delivery of a fluid to the external surface and interior surface of the catheter in the fashion, and for the purposes, described hereinbefore.

It should be further noted that the shape and diameter of the individual tubes and/or apertures, and the fluid pressures selected, are generally functions of design choice and/or of the application to which the catheter will be applied, and the constructions illustrated and described herein are not intended to limit the functionality of the device with respect to its beneficial properties. It should be further understood that those features and elements of the alternative embodiments not shown in FIGS. 7, 8 and 9 may be in accordance with the other embodiments shown in FIGS. 1 to 6 and described herein.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, however, therefore, to be limited only as indicated by the scope of the claims appended hereto.

What is claimed is:

1. A catheter insertable into a body for establishing a fluid communication path between a location external to the body and a site within the body, said catheter comprising:

a first elongated tube;

a second elongated tube disposed longitudinally within said first tube, said first tube having a portion sized so as to fluid-tightly sealingly engage said second tube, said first and second tubes defining therebetween a coaxial channel extending longitudinally along and within said first tube to define a first fluid communication path through which a first fluid is deliverable;

said second tube defining therewithin a second fluid communication path through and along which a second fluid is flowable between a location external to the body and a site within the body; and said second tube having defined therethrough a plurality of predeterminately-sized apertures for delivering said first fluid from said channel to an interior portion of said second tube for allowing selective irrigation of said interior portion with the first fluid so as to discourage accumulations of unwanted matter on an interior surface of the second tube.

2. The catheter according to claim 1, wherein said plural predeterminately-sized apertures are disposed circumferentially about and longitudinally along said second tube.

3. The catheter according to claim 1, wherein said plural predeterminately-sized apertures are sized and disposed for predeterminately controlling the flow of the first fluid through said apertures such that as the first fluid is delivered from said channel into the second tube through said apertures, the first fluid remains substantially on and along the interior surface of said second tube so as to substantially coat said interior surface of the second tube with the first fluid.

4. The catheter according to claim 1, wherein said plural predeterminately-sized apertures are sized and disposed for predeterminately controlling the flow of the first fluid through said apertures such that as the first fluid is delivered under pressure from said channel through said apertures, the first fluid substantially flushes the second fluid communication path of said second tube.

5. The catheter according to claim 1, wherein said first tube comprises a distal end portion operatively insertable into the body, an opening defined at said first tube distal end portion, said second tube having a distal end portion insertable into the body through said first tube distal end opening, said first tube distal end opening being sized so as to fluid-tightly sealingly engage said second tube, said distal end of said second tube being capable of extension beyond the distal end of said first tube, said first and second tubes being longitudinally movable relative to each other for selective adjustment of the extension of said second tube outwardly beyond said first tube distal end through said first tube distal end opening.

6. The catheter according to claim 5, wherein said plural predeterminately-sized apertures are disposed circumferentially around and longitudinally along said second tube.

7. The catheter according to claim 5, wherein said plural predeterminately-sized apertures are sized and disposed for predeterminately controlling the flow of the first fluid through said apertures such that as the first fluid is delivered from said channel through said aperture, the first fluid remains substantially on and along the interior surface of said second tube so as to substantially coat said interior surface of the second tube with the first fluid.

8. The catheter according to claim 5, wherein said plural predeterminately-sized apertures are sized and disposed for predeterminately controlling the flow of the first fluid through said apertures such that as the first fluid is delivered under pressure from said channel through said apertures, the first fluid substantially flushes the second tube so as to prevent the accumulation of unwanted matter on and along the interior surface of said second tube.

9. The catheter according to claim 1, wherein said first fluid is selected from a group consisting of a non-specific anti-microbial short chain fatty acid, saline, free water, a liquid lubricant, an anti-coagulant liquid and heparin.

10. The catheter according to claim 1, wherein said apertures are substantially circular in cross-section.

11. The catheter according to claim 1, wherein said apertures are shaped as elongated slits oriented substantially along the longitudinal axis of said second tube.

12. The catheter according to claim 1, wherein said apertures are shaped as elongated slits oriented at an angle substantially transverse to the longitudinal axis of said second tube.

13. The catheter according to claim 1, wherein said first tube includes a plurality of predeterminately-sized secondary apertures defined therein for delivering the first fluid outwardly from said channel to an outer surface of said first tube.

14. The catheter of claim 13, wherein said predetermined size of said secondary apertures is selected for predeterminately controlling the flow of the first fluid through said secondary apertures so that as the first fluid is delivered outwardly from said channel through said secondary apertures, the first fluid remains substantially on and along the outer peripheral surface of said first tube so as to coat said first tube peripheral surface with the first fluid and thereby create a fluid barrier on and along the first tube peripheral surface disposed within the body.

15. The catheter according to claim 1, wherein each of said tubes is flexible.

16. In combination:
a device insertable into a body for establishing a fluid communication path between a location external to the body and a site within the body, said device comprising:
a catheter comprising a first elongated tube capable of insertion into the body, said first tube having an outer peripheral surface;
a second elongated tube disposed longitudinally within said first tube, said first tube having an opening sized so as to fluid-tightly sealingly engage said second tube, said first and second tubes defining therebetween a channel extending longitudinally along and within said first tube to define a fluid communication path; and
a fluid deliverable through said fluid communication path and deliverable from said fluid communication path through a plurality of predeterminately-sized apertures defined in and through said first tube and said second tube for delivering said first fluid from said channel to an outer surface of said first tube and to an interior portion of said second tube.

17. A method for introducing fluid to exterior and interior surfaces of a catheter to reduce medical risks normally associated with catheter placement in the body, comprising the steps of:
inserting, into the body, a first tube and a second tube disposed within the first tube to create a longitudinal channel defined coaxially between the first and second tubes;
delivering a fluid through said channel and outwardly from said channel through a plurality of apertures defined in said first tube and through a plurality of apertures in said second tube so that said fluid is simultaneously delivered to the exterior surface of said first tube and to the interior of said second tube.

18. The method according to claim 17, wherein said step of delivering fluid comprises delivering a fluid selected from a group consisting of a non-specific anti-microbial short chain fatty acid, saline, free water, a liquid lubricant, an anti-coagulant solution and heparin.

19. A method for introducing fluid to exterior and interior surfaces of a catheter to reduce medical risks normally associated with catheter placement in the body, comprising the steps of:
inserting, into the body, a first tube and a second tube disposed within the first tube to create a longitudinal channel defined coaxially between the first and second tubes;
delivering a fluid through said channel and outwardly from said channel through a plurality of capillary apertures defined in said first tube and predeterminately sized so that as the fluid is delivered outwardly through said capillary apertures from said channel the fluid remains substantially on and along the outer peripheral surface of the first tube so as to coat the first tube outer peripheral surface with the fluid and thereby create an anti-infective barrier along the outer peripheral surface of the first tube within the body; and
simultaneously delivering the fluid through a plurality of predeterminately-sized openings defined in and through said second tube for delivering the fluid from said channel to an interior portion of said second tube so as to provide selective irrigation of said second tube interior portion with the fluid so as to prevent the accumulation of unwanted matter on and along the interior surface of said second tube.

20. The method according to claim 19, wherein said steps of delivering fluid comprises delivering a fluid selected from a group consisting of a non-specific anti-microbial short chain fatty acid, saline, free water, a liquid lubricant, an anti-coagulant solution and heparin.

* * * * *